United States Patent [19]

Lewis et al.

[11] Patent Number: 4,497,908

[45] Date of Patent: Feb. 5, 1985

[54] COPPER-ALKALI METAL-RUTHENIUM/SILICA CATALYST FOR CONVERTING SYNGAS TO LINEAR ALPHA-OLEFINS

[75] Inventors: Robert M. Lewis, Houston; Lynn H. Slaugh, Cypress, both of Tex.

[73] Assignee: Shell Oil Company, Houston, Tex.

[21] Appl. No.: 529,673

[22] Filed: Mar. 23, 1984

[51] Int. Cl.³ .................. B01J 21/08; B01J 23/58; B01J 23/72

[52] U.S. Cl. ................................ 502/245; 518/713

[58] Field of Search ................... 502/245; 518/713

[56] References Cited

U.S. PATENT DOCUMENTS 4,377,643  3/1983  Pesa et al. ................ 502/245 X

Primary Examiner—W. J. Shine

[57] ABSTRACT

A copper-alkali metal-ruthenium supported on silica catalyst is utilized in syngas reactions to produce linear alpha-olefins in high yield.

5 Claims, No Drawings

COPPER-ALKALI METAL-RUTHENIUM/SILICA CATALYST FOR CONVERTING SYNGAS TO LINEAR ALPHA-OLEFINS

FIELD OF THE INVENTION

This invention relates to a catalyst composition comprising alkali metal, copper and ruthenium on a silica support. These catalysts are useful in syngas reactions to produce olefins, particularly linear alpha-olefins.

BACKGROUND OF THE INVENTION

Supported ruthenium catalysts have been utilized in syngas reactors. Okuhara et al (J.C.S. Chem. Comm., pp. 1114–1115, 1981) discloses the use of alkali metal promoted ruthenium supported catalysts for the production of olefins from syngas.

SUMMARY OF THE INVENTION

The instant invention comprises copper-alkali metal-ruthenium supported on silica catalysts which are utilized in syngas reactions to prepare linear alpha-olefins in high yield. The catalysts of the instant invention are prepared by impregnating the porous silica support with a solution of soluble copper, alkali metal and ruthenium salts, drying and calcining the impregnated silica and subsequently reducing the calcined material. Material prepared by the simultaneous deposition of the three metal salts produces a higher proportion of linear alpha-olefins than materials prepared in alternate fashions, as for example, sequential deposition of individual metal salts.

DESCRIPTION OF THE PREFERRED EMBODIMENT

The present invention comprises a catalyst composition and its use in syngas reactions, particularly its use to convert syngas (a mixture of carbon monoxide and hydrogen) to linear alpha-olefins in high yield. The catalyst composition comprises a copper-alkali metal-ruthenium catalyst supported on a silica support prepared by a process which comprises:

(a) impregnating a porous silica support with a solution of soluble copper, alkali metal and ruthenium salts, (b) drying and calcining the impregnated support in an oxidizing or neutral atmosphere at a temperature ranging from about 200° C. to about 800° C., preferably from about 300° C. to about 600° C., and then (c) reducing the impregnated support in a reducing atmosphere at a temperature ranging from about 200° C. to about 800° C., and preferably from about 300° C. to about 600° C.

The porous silica supports that are used in the preparation of the instant catalysts are readily available commercially and are known as silica gels which are essentially substantially dehydrated amorphous silica. These materials are available in various density grades, from low density with surface area ranging from about 100-200 m²/g, to regular density with surface areas up to about 800 m²/g. These commercially available materials are used as desiccants, selective adsorbents, catalysts and catalyst supports. The porous silica may contain minor proportions of other materials without departing from the scope of the invention such as for example, alumina and carbon. Examples of commercially available silica gels and their properties are shown in the table below.

| Support | Surface Area, $m^2/g$ | Pure Vol, cc/g | Density g/cc | Particle Size |
|---|---|---|---|---|
| Davison* Grade 952 $SiO_2$ | 300 | 1.65 | | 70 mesh (avg) |
| Davison Grade 57 $SiO_2$ | 300 | 1.0 | | <100 mesh |
| Davison Grade 03 $SiO_2$ | 750 | 0.43 | 0.7 | |

*Manufactured by Davison Chemical Div., W. R. Grace & Co.

Frequently the porous silica carrier will typically be dried to remove adsorbed moisture, particularly when a non-aqueous solvent is utilized in the impregnation step.

A critical aspect of the instant invention is that the three salts comprising the catalytic metals, copper, alkali-metal, and ruthenium, will be utilized dissolved in a single solution. Thus, simultaneous impregnation is effected, rather than a sequential impregnation of individual salts. This simultaneous impregnation with the three metallic components provides a catalyst that when utilized in the syngas reaction, produces a higher proportion of linear alpha-olefins than does the use of a catalyst prepared by individual impregnation of the metal components.

The first step is to dissolve suitable salts in a suitable solvent. The solvent should be one that will suitably dissolve the salts of choice. Preferably the solvent will be an aqueous solvent, possibly acidic or basic. Optionally, the solvent may be an organic solvent, such as for example, an alcohol or an ether.

Illustrative of suitable copper salts would include the nitrates, the halides, the oxalates, the carboxylates and the like. Suitable alkali-metal salts would include the halides, the sulfates, the nitrates, the oxalates, the carboxylates, and the like. Lithium salts are preferred illustrative examples of suitable ruthenium salts include salts such as ruthenium (III) chloride hydrate, ruthenium (III) bromide, anhydrous ruthenium (III) chloride and ruthenium nitrate. Also suitable are the ammonia complexes of the ruthenium halide such as for example $Ru(NH_3)_6Cl_3$ and $Ru(NH_3)_6I_3$. Salts of suitable organic acids are also suitable. Here, examples include ruthenium (III) acetate, ruthenium (III) propionate, ruthenium hexafluoracetylacetoneate, ruthenium (III) triofuorocetate, ruthenium octanoate, ruthenium naphthenate, ruthenium valerate, and ruthenium (III) acetylacetoneate.

Suitable salts and solvents are readily chosen by one having skill in the art by utilizing simple and routine experimentation.

After dissolution of the salts in an appropriate solvent, the solution is then utilized to impregnate the porous silica support. A preferred impregnation method is the so-called "dry" impregnation method wherein just that amount of solution is used which will just wet the silica, although greater or lesser amounts of solution can be utilized.

After impregnation the material is dried and calcined. Frequently, the drying step is combined with the calcining step. The calcining is carried out in an oxidizing or neutral atmosphere. Suitable oxidizing atmospheres are air and oxygen. Suitable neutral atmospheres are nitrogen and helium. Calcination is carried out at a temperature ranging from about 200° C. to about 800° C., preferably from about 300° C. to about 600° C.

The next step is to reduce the calcined material in a reducing atmosphere. Suitable reducing atmospheres comprise those containing for example hydrogen or carbon monoxide. A hydrogen-containing atmosphere is the prefered reducing atmosphere. This prefered atmosphere can be either pure hydrogen or can be hydrogen diluted with suitable inert gas such as nitrogen or helium. Reduction is carried out at a temperature ranging from about 200° C. to about 800° C., preferably from about 300° C. to about 600° C.

Calcination and reduction times are not critical and may vary over a wide range. The times will vary according to the temperature, higher temperatures will require shorter times and vice versa. Times will typically range from about 1 hour to about 200 hours.

The concentration of the copper found in the finished catalyst product will range from about 0.01 to about 5, preferably from about 0.1 to about 3% by wt measured as the metal. The amount of alkali-metal present in the finished catalyst will range from about 0.015 to about 1.5, preferably from about 0.075 to about 0.75 gram equivalent weights per kilogram of total catalyst. Lithium is a preferred alkali metal. The amounts of ruthenium present in the finished catalyst product will range from about 1 to about 20, preferably from about 5 to about 15% by weight measured as the metal. The metals found in the catalyst will be found in various oxidized and/or reduced states, depending upon the degree of calcination and reduction to which the metals were subjected.

The catalyst is used in a fashion typical of that used for heterogeneous catalysts. It may be used in fixed beds, in fluidized beds or in batch reactors. Typical syngas reaction temperatures range from about 300° C. to about 450° C. and pressures typically range from about 1 to about 500 bar. Typical feed rates include gaseous hourly space velocities ranging from about 500 to about 10,000 1/1/hr. A wide range of carbon monoxide to hydrogen can be used in the feed. For example, a $CO:H_2$ ratio ranging from about 1:2 to about 3:1 is generally suitable.

The product of the instant process comprises hydrocarbons having a large proportion of linear alpha-olefins.

The process of the instant invention, including preparation of the catalyst composition and its use in a syngas reaction will be further described below by the following illustrative embodiments which are provided for illustration and are not to be construed as limiting the invention.

ILLUSTRATIVE EMBODIMENTS

Catalysts were prepared by the dry impregnation of calcined Davison 57 grade silica with an aqueous solution of $RuCl_3$, $CuCl_2$ and $LiCl$. The impregnated materials were then calcined in a nitrogen atmosphere at temperature of about 400°–500° C. and reduced in a flow reactor with hydrogen at about 900 psi and temperatures of about 400°–500° C. for times ranging from about 30–100 hours. A catalyst of this invention containing Ru, Cu and Li is tested in the table below as Catalyst 1. Comparative catalysts containing, Ru, Ru+Cu and Ru+Li are shown in the table below as catalysts A, B and C, respectively. Catalyst D was prepared by first impregnating with a LiCl solution, calcining, reimpregnating with $CuCl_2$ and $RuCl_3$, calcining and then reducing.

The catalysts were tested with syngas (1:1) at 900 psig (3000 (GHSV) and 320° C. A 1.4 cm I.D. high pressure 316 stainless steel tubular reactor was utilized. Silicon carbide chips (15 ml each) were used above and below the catalyst (10 ml) to support it in the center of the reactor. The product of the reaction was analyzed and the result is given in the following table.

| Catalyst | Composition (% w) | Total Conversion Percent | Conversion to $CO_2$ Percent | Selectivity percent[1] | | | Olefin yield[3] |
| --- | --- | --- | --- | --- | --- | --- | --- |
| | | | | Methane | Paraffins | Olefins[2] | |
| 1 | 7.8 Ru; 0.08 Cu, 0.27 Li | 51 | 4 | 5 | 25 | 67 | 34 |
| A | 6.0 Ru | 71 | 28 | 88 | 92 | 7 | 5 |
| B | 6.8 Ru; 0.46 Cu | 36 | 2 | 14 | 43 | 56 | 20 |
| C | 7.3 Ru; 0.28 Li | 31 | 3 | 8 | 37 | 55 | 17 |
| D | 6.6 Ru; 0.17 Cu; 0.26 Li | 35 | 1 | 4 | 35 | 59 | 21 |

[1]Selectivity is based on organic products (Not $CO_2$). Unaccounted selectivity percent is due to oxygenates.
[2]Linear α-olefins.
[3]Conversion multiplied by olefin selectivity percent divided by 100.

We claim:
1. A copper-alkali metal-ruthenium supported on silica catalyst composition useful for converting syngas to linear alpha-olefins in high yields which catalyst is prepared by a process which comprises:
   (a) impregnating a porous silica support with a solution consisting essentially of soluble copper, alkali metal and ruthenium salts,
   (b) drying and calcining the impregnated support in an oxidizing or neutral atmosphere at a temperature ranging from about 200° C. to about 800° C., and then
   (c) reducing the impregnated support in a reducing atmosphere at a temperature ranging from about 200° C. to about 800° C.

2. The catalyst of claim 1 wherein the calcination takes place at a temperature ranging from about 300° C. to about 600° C. and the reduction takes place at a temperature ranging from about 300° C. to about 600° C.

3. The catalyst of claim 1 wherein the concentration of the copper ranges from about 0.01 to about 5 percent by weight, the alkali metal ranges from about 0.015 to about 1.5 gram equivalent weights per kilogram of total catalyst and the ruthenium ranges from about 1 to about 20 percent by weight.

4. The catalyst of claim 3 wherein the copper ranges from about 0.1 to about 3 percent by weight, the alkali metal ranges from about 0.075 to about 0.75 gram equivalent weights per kilogram and the ruthenium ranges from about 5 to about 15 percent.

5. The catalyst of claims 1, 2, 3 or 4 wherein the alkali metal is lithium.

* * * * *

UNITED STATES PATENT AND TRADEMARK OFFICE
CERTIFICATE OF CORRECTION

PATENT NO. : 4,497,908
DATED : February 5, 1985
INVENTOR(S) : ROBERT M. LEWIS and LYNN H. SLAUGH It is certified that error appears in the above-identified patent and that said Letters Patent are hereby corrected as shown below:

On the cover page of the patent at [21], the Application Number should read 592,673.

Signed and Sealed this

Eighteenth Day of June 1985

[SEAL]

Attest:

DONALD J. QUIGG

Attesting Officer

Acting Commissioner of Patents and Trademarks